United States Patent
Zhang

(10) Patent No.: US 11,977,838 B2
(45) Date of Patent: May 7, 2024

(54) SYNONYM MINING METHOD, APPLICATION METHOD OF SYNONYM DICTIONARY, MEDICAL SYNONYM MINING METHOD, APPLICATION METHOD OF MEDICAL SYNONYM DICTIONARY, SYNONYM MINING DEVICE AND STORAGE MEDIUM

(71) Applicant: BOE TECHNOLOGY GROUP CO., LTD., Beijing (CN)

(72) Inventor: Zhenzhong Zhang, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 416 days.

(21) Appl. No.: 17/419,355

(22) PCT Filed: Nov. 5, 2020

(86) PCT No.: PCT/CN2020/126653
§ 371 (c)(1),
(2) Date: Jun. 29, 2021

(87) PCT Pub. No.: WO2021/109787
PCT Pub. Date: Jun. 10, 2021

(65) Prior Publication Data
US 2022/0083733 A1 Mar. 17, 2022

(30) Foreign Application Priority Data

Dec. 5, 2019 (CN) .......................... 201911234262.3

(51) Int. Cl.
G06F 40/247 (2020.01)
G06F 16/335 (2019.01)
G06F 16/35 (2019.01)
G06F 16/36 (2019.01)
(Continued)

(52) U.S. Cl.
CPC .......... G06F 40/247 (2020.01); G06F 16/335 (2019.01); G06F 16/353 (2019.01);
(Continued)

(58) Field of Classification Search
CPC .... G06F 40/247; G06F 16/353; G06F 16/374; G06F 16/335; G06F 40/242; G06F 40/295; G16H 50/70
See application file for complete search history.

(56) References Cited

U.S. PATENT DOCUMENTS 11,783,950 B2 * 10/2023 Pauly ..................... G16H 15/00
705/3
2015/0120735 A1 4/2015 Tsuchida et al.
(Continued)

FOREIGN PATENT DOCUMENTS

CN 102955857 A 3/2013
CN 103377239 A 10/2013
(Continued)

Primary Examiner — Mohammad K Islam
(74) Attorney, Agent, or Firm — Chiwin Law LLC

(57) ABSTRACT

Disclosed are a synonym mining method, an application method of a synonym dictionary, a medical synonym mining method, an application method of a medical synonym dictionary, a synonym mining device and a storage medium. The synonym mining method includes: performing a recognition process on corpus data to obtain a named entity set of at least one category, wherein the named entity set of each category includes a plurality of named entities; performing a clustering process on the plurality of named entities in the named entity set of the each category to obtain a synonym candidate set corresponding to the each category; and performing, based on a word from similarity and a context similarity, a filtering process on the synonym candidate set corresponding to the each category to obtain a synonym set corresponding to the each category.

18 Claims, 3 Drawing Sheets

(51) Int. Cl.
　　　*G06F 40/242*　　　(2020.01)
　　　*G06F 40/295*　　　(2020.01)
　　　*G16H 50/70*　　　(2018.01)

(52) U.S. Cl.
　　　CPC .......... *G06F 16/374* (2019.01); *G06F 40/242* (2020.01); *G06F 40/295* (2020.01); *G16H 50/70* (2018.01)

(56) References Cited

U.S. PATENT DOCUMENTS

| | | | |
|---|---|---|---|
| 2021/0109995 A1* | 4/2021 | Mihindukulasooriya | ................... G06F 40/247 |
| 2023/0316408 A1* | 10/2023 | Khan | ................ G06Q 40/08 705/2 |

FOREIGN PATENT DOCUMENTS

| | | | | |
|---|---|---|---|---|
| CN | 104281565 A | | 1/2015 | |
| CN | 105447158 A | | 3/2016 | |
| CN | 106649783 A | | 5/2017 | |
| CN | 108052509 A | | 5/2018 | |
| CN | 109002432 A | | 12/2018 | |
| CN | 109117436 A | | 1/2019 | |
| CN | 110019806 A | | 7/2019 | |
| CN | 110020438 A | * | 7/2019 | ........... G06F 17/278 |
| CN | 110442726 A | | 11/2019 | |
| CN | 110991168 A | | 4/2020 | |
| CN | 111625659 A | * | 9/2020 | ........... G06F 16/367 |
| CN | 112840336 A | * | 5/2021 | ....... G06F 16/24573 |
| WO | WO-2020193966 A1 | * | 10/2020 | ........... G06F 40/295 |

* cited by examiner

SYNONYM MINING METHOD, APPLICATION METHOD OF SYNONYM DICTIONARY, MEDICAL SYNONYM MINING METHOD, APPLICATION METHOD OF MEDICAL SYNONYM DICTIONARY, SYNONYM MINING DEVICE AND STORAGE MEDIUM

This application is a U.S. National Phase Entry of International Application No. PCT/CN2020/126653 filed on Nov. 5, 2020, designating the United States of America and claiming priority to Chinese Patent Application No. 201911234262.3, filed on Dec. 5, 2019. The present application claims priority to and the benefit of the above-identified applications and the above-identified applications are incorporated by reference herein in their entirety.

TECHNICAL FIELD

Embodiments of the present disclosure relate to a synonym mining method, an application method of a synonym dictionary, a medical synonym mining method, an application method of a medical synonym dictionary, a synonym mining device, and a storage medium.

BACKGROUND

The natural language processing (NLP) field is an interdisciplinary field related to computer science, artificial intelligence and information engineering, involving knowledge of statistics, linguistics, etc. The goal of NLP is to enable a computer to process or "understand" natural language, so as to perform tasks such as text classification, language translation, question answering, etc. As the basic elements of natural language, words are crucial to natural language processing.

SUMMARY

At least one embodiment of the present disclosure provides a synonym mining method, which includes: performing a recognition process on corpus data to obtain a named entity set of at least one category, wherein the named entity set of each category includes a plurality of named entities; performing a clustering process on the plurality of named entities in the named entity set of the each category to obtain a synonym candidate set corresponding to the each category; and performing, based on a word form similarity and a context similarity, a filtering process on the synonym candidate set corresponding to the each category to obtain a synonym set corresponding to the each category.

For example, in the synonym mining method provided by some embodiments of the present disclosure, the synonym candidate set includes a plurality of synonym candidate clusters, and each of the plurality of synonym candidate clusters includes a plurality of named entities; and the performing the filtering process on the synonym candidate set includes: performing the filtering process on the plurality of named entities in each of the plurality of synonym candidate clusters.

For example, in the synonym mining method provided by some embodiments of the present disclosure, the performing the filtering process on the plurality of named entities in the each of the plurality of synonym candidate clusters includes: randomly sorting the plurality of named entities in the each of the plurality of synonym candidate clusters to obtain a sorted candidate cluster set $\{e_i\}$, where $e_i$ represents an i-th named entity, i is an integer, $1 \leq i \leq K$, and K is a count of the named entities in the each of the plurality of synonym candidate clusters; taking a first named entity $e_i$ as a first sub-cluster; and determining whether an m-th named entity $e_m$ can be added to one of existing n sub-clusters, if the m-th named entity $e_m$ can be added to a certain existing sub-cluster, adding the m-th named entity $e_m$ to the certain existing sub-cluster, and if the m-th named entity $e_m$ cannot be added to any existing sub-cluster, taking the m-th named entity $e_m$ as a new sub-cluster, where m takes a value of 2, 3, ..., and K in turn, and n is a count of existing sub-clusters in a case where the m-th named entity is determined.

For example, in the synonym mining method provided by some embodiments of the present disclosure, the determining whether the m-th named entity $e_m$ can be added to one of the existing n sub-clusters includes: determining whether the m-th named entity $e_m$ can be added to an existing j-th sub-cluster, where j takes a value of 1, 2, ..., and n in turn; and the determining whether the m-th named entity $e_m$ can be added to the existing j-th sub-cluster includes: calculating a word form similarity and a context similarity between the m-th named entity $e_m$ and each named entity in the existing j-th sub-cluster, wherein if a proportion of named entities, which satisfy a predetermined relationship with the m-th named entity $e_m$ in terms of the word form similarity and the context similarity, in the existing j-th sub-cluster, reaches a predetermined proportion threshold, the m-th named entity $e_m$ can be added to the j-th sub-cluster, or else, the m-th named entity $e_m$ cannot be added to the j-th sub-cluster.

For example, in the synonym mining method provided by some embodiments of the present disclosure, the predetermined relationship is expressed as:

$$(S_1(e_a,e_b))^2 + (S_2(e_a,e_b))^2 \geq 1$$

where $S_1(e_a, e_b)$ represents a word form similarity between any two named entities $e_a$ and $e_b$, and $S_2(e_a, e_b)$ represents a context similarity between the any two named entities $e_a$ and $e_b$.

For example, in the synonym mining method provided by some embodiments of the present disclosure, the word form similarity between the any two named entities $e_a$ and $e_b$ is expressed as:

$$S_1(e_a, e_b) = 1 - \frac{dis(e_a, e_b)}{\max(len(e_a), len(e_b))},$$

where $S_1(e_a, e_b)$ represents the word form similarity, $dis(e_a, e_b)$ represents a minimum edit distance between the two named entities $e_a$ and $e_b$, $len(e_a)$ represents a word length of the named entity $e_a$, $len(e_b)$ represents a word length of the named entity $e_b$, and $\max(len(e_a), len(e_b))$ represents a maximum of $len(e_a)$ and $len(e_b)$.

For example, in the synonym mining method provided by some embodiments of the present disclosure, the context similarity between the any two named entities $e_a$ and $e_b$ is expressed as:

$$S_2(e_a, e_b) = \frac{p(e_b \mid e_a) + p(e_a \mid e_b)}{2},$$

where $S_2(e_a, e_b)$ represents the context similarity, $p(e_b|e_a)$ represents a probability of generating the named entity $e_b$ form the named entity $e_a$, and $p(e_a|e_b)$ represents a probability of generating the named entity $e_a$ from the named entity $e_b$.

For example, in the synonym mining method provided by some embodiments of the present disclosure, the probability $p(e_b|e_a)$ of generating the named entity $e_b$ form the named entity $e_a$ and the probability $p(e_a|e_b)$ of generating the named entity $e_a$ from the named entity $e_b$ are respectively expressed as:

$$p(e_b|e_a) = \sum_{u \in C(e_a)} p(u|e_a)p(e_b|u),$$

$$p(e_a|e_b) = \sum_{v \in C(e_b)} p(v|e_b)p(e_a|v),$$

where $C(e_a)$ represents a context information set of the named entity $e_a$, u represents a word element in $C(e_a)$, $p(u|e_a)$ represents a probability of generating the word element u from the named entity $e_a$, $p(e_b|u)$ represents a probability of generating the named entity $e_b$ from the word element u, $C(e_b)$ represents a context information set of the named entity $e_b$, v represents a word element in $C(e_b)$, $p(v|e_b)$ represents a probability of generating the word element v from the named entity $e_b$, and $p(e_a|v)$ represents a probability of generating the named entity $e_a$ from the word element v.

For example, in the synonym mining method provided by some embodiments of the present disclosure, the probability $p(u|e_a)$ of generating the word element u from the named entity $e_a$, the probability $p(e_b|u)$ of generating the named entity $e_b$ from the word element u, the probability $p(v|e_b)$ of generating the word element v from the named entity $e_b$, and the probability $p(e_a|v)$ of generating the named entity $e_a$ from the word element v are respectively expressed as:

$$p(u|e_a) = \frac{\text{count}(u, e_a)}{\text{count}(e_a)},$$

$$p(e_b|u) = \frac{\text{count}(e_b, u)}{\text{count}(u)},$$

$$p(v|e_b) = \frac{\text{count}(v, e_b)}{\text{count}(e_b)},$$

$$p(e_a|v) = \frac{\text{count}(e_a, v)}{\text{count}(v)},$$

where count($e_a$) represents a count of sentences including the named entity $e_a$ in the corpus data, count($e_b$) represents a count of sentences including the named entity $e_b$ in the corpus data, count(u) represents a count of sentences including the word element u in the corpus data, count(v) represents a count of sentences including the word element v in the corpus data, count(u, $e_a$) represents a count of sentences including both the word element u and the named entity $e_a$ in the corpus data, count($e_b$, u) represents a count of sentences including both the named entity $e_b$ and the word element u in the corpus data, count(v, $e_b$) represents a count of sentences including both the word element v and the named entity $e_b$ in the corpus data, and count($e_a$, v) represents a count of sentences including both the named entity $e_a$ and the word element v in the corpus data.

For example, in the synonym mining method provided by some embodiments of the present disclosure, the predetermined proportion threshold is in the range of 70% to 90%.

For example, in the synonym mining method provided by some embodiments of the present disclosure, before the performing the recognition process on the corpus data, the synonym mining method further includes: performing a sentence segmentation process on the corpus data to segment the corpus data into a plurality of sentences.

For example, in the synonym mining method provided by some embodiments of the present disclosure, the performing the recognition process on the corpus data includes: performing, based on the plurality of sentences, the recognition process by using one of a conditional random field model and a maximum entropy Markov model.

For example, in the synonym mining method provided by some embodiments of the present disclosure, before the performing the recognition process on the corpus data, the synonym mining method further includes: performing an error word correction process on the corpus data to correct error words in the corpus data.

For example, in the synonym mining method provided by some embodiments of the present disclosure, the performing the clustering process on the plurality of named entities in the named entity set of the each category includes: based on all named entities in the named entity set, performing word segmentation on the corpus data and removing a stop word, so as to collect a context information set of each of the plurality of named entities; combining context information sets of all the named entities in the named entity set to obtain an overall context information set of the named entity set; conveying, based on the overall context information set of the named entity set, each of the plurality of named entities in the named entity set as an overall context information vector; and performing, based on the overall context information vector of the each of the plurality of named entities in the named entity set, the clustering process on all the named entities in the named entity set.

For example, in the synonym mining method provided by some embodiments of the present disclosure, the overall context information set of the named entity set is expressed as $\{x_t\}$, where $x_t$ represents a t-th word element in the overall context information set of the named entity set, t is an integer, $1 \leq t \leq T$, and T is a count of word elements in the overall context information set of the named entity set; and the conveying, based on the overall context information set of the named entity set, each of the plurality of named entities in the named entity set as the overall context information vector, includes: calculating a weight $y_t$ of the t-th word element $x_t$ in the overall context information set $\{x_t\}$ with respect to the each of the plurality of named entities, where t takes a value of 1, 2, . . . , and T in turn, and obtaining an overall context information vector ($y_1$, $y_2$, . . . , $y_T$) of the each of the plurality of named entities.

For example, in the synonym mining method provided by some embodiments of the present disclosure, a calculation formula of the weight $y_t$ of the t-th word element $x_t$ with respect to the each of the plurality of named entities is expressed as:

$$y_t = \frac{\text{count}(E, x_t)}{\text{count}(x_t)},$$

where E represents the each of the plurality of named entities, count($x_t$) represents a count of sentences including the t-th word element $x_t$ in the corpus data, and count(E, $x_t$) represents a count of sentences including both the named entity E and the t-th word element $x_t$ in the corpus data.

For example, in the synonym mining method provided by some embodiments of the present disclosure, the performing, based on the overall context information vector of the each of the plurality of named entities in the named entity set, the clustering process on all the named entities in the named entity set, includes: taking each of the plurality of named entities in the named entity set as a candidate cluster, and taking the overall context information vector of the each of the plurality of named entities as a center vector of a corresponding candidate cluster; and performing the clustering process on all current candidate clusters until all the current candidate clusters cannot continue to be clustered, wherein the performing the clustering process on all the current candidate clusters includes: calculating an entity similarity between every two candidate clusters among all the current candidate clusters; determining whether a maximum value of the entity similarities reaches a predetermined threshold; if the maximum value of the entity similarities reaches the predetermined threshold, clustering two candidate clusters corresponding to the maximum value of the entity similarities into a new candidate cluster, taking an average of overall context information vectors of all named entities in the new candidate cluster as a center vector of the new candidate cluster, taking the new candidate cluster and remaining candidate clusters as all current candidate clusters, and continuing to perform the clustering process on all the current candidate clusters; and if the maximum value of the entity similarities does not reach the predetermined threshold, determining that all the current candidate clusters cannot continue to be clustered.

For example, in the synonym mining method provided by some embodiments of the present disclosure, a calculation formula of an entity similarity between any two candidate clusters is expressed as:

$$Sim(F_1, F_2) = \frac{V(F_1) \cdot V(F_2)}{|V(F_1)| \times |V(F_2)|},$$

where $V(F_1)$ and $V(F_2)$ represent center vectors of the any two candidate clusters, respectively, $V(F_1) \cdot V(F_2)$ represents a dot product of the center vectors $V(F_1)$ and $V(F_2)$ of the any two candidate clusters, and $|V(F_1)|$ and $|V(F_2)|$ represent modulus of the center vectors $V(F_1)$ and $V(F_2)$ of the any two candidate clusters, respectively.

For example, in the synonym mining method provided by some embodiments of the present disclosure, the predetermined threshold is in the range of 0.7 to 0.9.

For example, the synonym mining method provided by some embodiments of the present disclosure further includes: constructing a synonym dictionary based on the synonym set corresponding to the each category.

For example, in the synonym mining method provided by some embodiments of the present disclosure, the corpus data includes medical text data.

At least one embodiment of the present disclosure further provides an application method of a synonym dictionary, wherein the synonym dictionary is constructed by using the synonym mining method provided by any one of the embodiments of the present disclosure, and the application method includes: according to the synonym dictionary, performing a normalization process on a plurality of named entities which are synonyms in at least one text data, so as to convey the plurality of named entities which are synonyms with one named entity among the plurality of named entities which are synonyms.

At least one embodiment of the present disclosure further provides a medical synonym mining method, which includes: performing a recognition process on medical corpus data to obtain a medical named entity set of at least one category, wherein the medical named entity set of each category includes a plurality of medical named entities; performing a clustering process on the plurality of medical named entities in the medical named entity set of the each category to obtain a medical synonym candidate set corresponding to the each category; and performing, based on a word form similarity and a context similarity, a filtering process on the medical synonym candidate set corresponding to the each category to obtain a medical synonym set corresponding to the each category.

For example, the medical synonyms mining method provided by some embodiments of the present disclosure further includes: constructing a medical synonym dictionary based on the medical synonym set corresponding to the each category.

At least one embodiment of the present disclosure further provides an application method of a medical synonym dictionary, wherein the medical synonym dictionary is constructed by using the medical synonym mining method provided by any one of the embodiments of the present disclosure, and the application method includes: according to the medical synonym dictionary, performing a normalization process on a plurality of medical named entities which are synonyms in at least one medical text data, so as to convey the plurality of medical named entities which are synonyms with one medical named entity among the plurality of medical named entities which are synonyms.

At least one embodiment of the present disclosure further provides a synonym mining device, which includes: a recognition processing module, configured to perform a recognition process on corpus data to obtain a named entity set of at least one category; a clustering processing module, configured to perform a clustering process on the named entity set of the each category to obtain a synonym candidate set corresponding to the each category; and a filtering processing module, configured to perform, based on a word form similarity and a context similarity, a filtering process on the synonym candidate set corresponding to the each category to obtain a synonym set corresponding to the each category.

For example, the synonym mining device provided by some embodiments of the present disclosure further includes: a dictionary constructing module, configured to construct a synonym dictionary based on the synonym set corresponding to the each category.

At least one embodiment of the present disclosure further provides a synonym mining device, which includes: a memory, configured to store computer readable instructions non-transitorily; and a processor, configured to execute the computer readable instructions, wherein upon the computer readable instructions being executed by the processor, the synonym mining method provided by any one of the embodiments of the present disclosure is executed.

At least one embodiment of the present disclosure further provides a storage medium, storing computer readable instructions non-transitorily, wherein upon the computer readable instructions being executed by a computer, the synonym mining method provided by any one of the embodiments of the present disclosure is executed.

BRIEF DESCRIPTION OF THE DRAWINGS

In order to clearly illustrate the technical solutions of the embodiments of the disclosure, the drawings of the embodiments will be briefly described in the following; it is obvious that the described drawings are only related to some embodiments of the disclosure and thus are not limitative to the disclosure.

DETAILED DESCRIPTION

Figure 1:
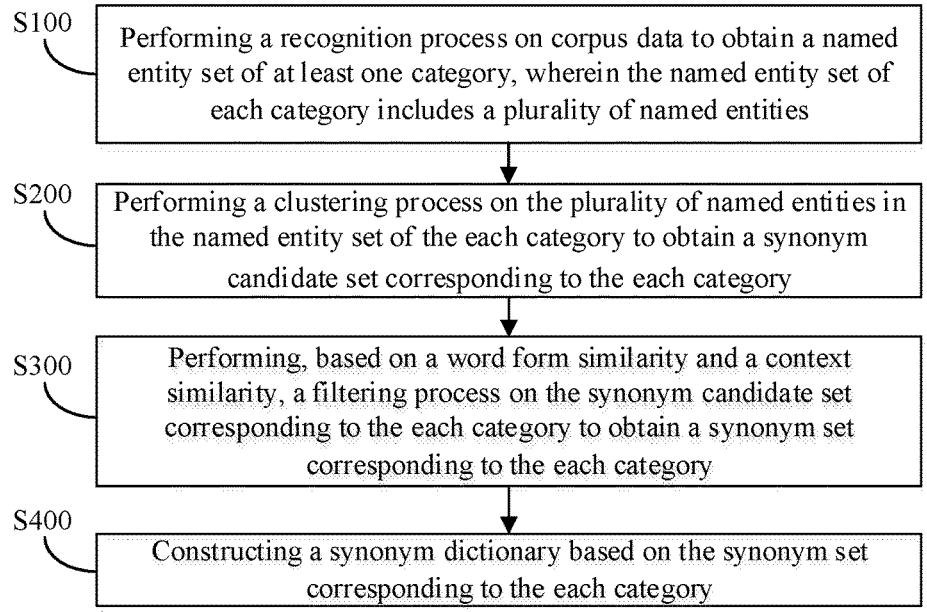
FIG. 1 is a flowchart of a synonym mining method provided by at least one embodiment of the present disclosure.

In order to make objects, technical details and advantages of the embodiments of the disclosure apparent, the technical solutions of the embodiments will be described in a clearly and fully understandable way in connection with the drawings related to the embodiments of the disclosure. Apparently, the described embodiments are just a part but not all of the embodiments of the disclosure. Based on the described embodiments herein, those skilled in the art can obtain other embodiment(s), without any inventive work, which should be within the scope of the disclosure.

Unless otherwise defined, all the technical and scientific terms used herein have the same meanings as commonly understood by one of ordinary skill in the art to which the present disclosure belongs. The terms "first," "second," etc., which are used in the present disclosure, are not intended to indicate any sequence, amount or importance, but distinguish various components. Also, the terms "comprise," "comprising," "include," "including," etc., are intended to specify that the elements or the objects stated before these terms encompass the elements or the objects and equivalents thereof listed after these terms, but do not preclude the other elements or objects. The phrases "connect", "connected", etc., are not intended to define a physical connection or mechanical connection, but may include an electrical connection, directly or indirectly. "On," "under," "right," "left" and the like are only used to indicate relative position relationship, and when the position of the object which is described is changed, the relative position relationship may be changed accordingly.

The present disclosure is described below with reference to some specific embodiments. In order to keep the following description of the embodiments of the present disclosure clear and concise, detailed descriptions of known functions and known components may be omitted. When any one component of an embodiment of the present disclosure appears in more than one of the accompanying drawings, the component is denoted by a same or similar reference numeral in each of the drawings.

With the geometric growth of electronic health data, how to use the medical big data to build a smart medical system has become an issue of concern. Due to the complexity of natural language, the phenomena of synonymy, polysemy, etc., are widespread in natural language. At the same time, there is no unified word specification to follow in the process of forming medical text data, so it often appears that the same medical entity (medical entity includes, for example, disease entity, drug entity, medical treatment entity, etc.) corresponds to different names in the massive medical text data (such as electronic medical records, medical literatures, etc.). For example, azithromycin (A-Qi-Mei-Su, in Chinese) is referred to as zithromax (Xi-Shu-Mei, in Chinese) in some literatures, and is further referred to as azithromycin (A-Qi-Mei-Su, in Chinese), azido-erythromycin (A-Qi-Hong-Mei-Su, in Chinese), erythromycin azide (Die-Dan-Hong-Mei-Su, in Chinese), etc., in other literatures. This phenomenon that the same medical entity has multiple expressions poses a huge obstacle to the automatic understanding and analysis of texts in the medical field. Therefore, normalizing the medical entity with multiple names to form a medical synonym dictionary is essential for analyzing medical data and understanding medical texts.

At least one embodiment of the present disclosure provides a synonym mining method, which includes: performing a recognition process on corpus data to obtain a named entity set of at least one category, wherein the named entity set of each category includes a plurality of named entities; performing a clustering process on the plurality of named entities in the named entity set of the each category to obtain a synonym candidate set corresponding to the each category; and performing, based on a word form similarity and a context similarity, a filtering process on the synonym candidate set corresponding to the each category to obtain a synonym set corresponding to the each category.

Some embodiments of the present disclosure further provide an application method of a synonym dictionary, a medical synonym mining method, an application method of a medical synonym dictionary, a synonym mining device, and a storage medium, which correspond to the synonym mining method described above.

The synonym mining method provided by at least one embodiment of the present disclosure can filter, based on the word form similarity and the context similarity, the synonym candidate set obtained by the clustering process, thereby improving the purity of the obtained synonym set, and further, a synonym dictionary can be constructed based on the obtained synonym set, so that the accuracy of knowledge filtering tasks, keyword extraction tasks, text classification tasks, semantic clustering tasks, or the like can be improved in the case where the synonym dictionary is applied to the natural language processing field.

Hereinafter, some embodiments of the present disclosure and examples thereof are described in detail with reference to the accompany drawings. It should be noted that the specific implementations being described here are merely used to illustrate and explain the present disclosure and thus are not limitative to the present disclosure.

FIG. 1 is a flowchart of a synonym mining method provided by at least one embodiment of the present disclosure. For example, the synonym mining method can be applied to a computing device, which include any electronic device with computing function, such as a smart phone, a laptop computer, a tablet computer, a desktop computer, a server, etc., and the embodiments of the present disclosure are not limited thereto. For example, the computing device can have a central processing unit (CPU) or a graphics processing unit (GPU), and the computing device can further include a memory. For example, the memory is a non-volatile memory (e.g., a read-only memory, ROM), and the code of an operating system is stored thereon. For example, the memory further stores codes or instructions, and by running these codes or instructions, the synonym mining method provided by the embodiments of the present disclosure can be implemented.

For example, as illustrated in FIG. 1, the synonym mining method includes steps S100 to S400.

Step S100: performing a recognition process on corpus data to obtain a named entity set of at least one category, wherein the named entity set of each category includes a plurality of named entities.

For example, in step S100, the corpus data can be corpus data oriented to a specific field, such as medical text data oriented to the medical field, biological text data oriented to the biological field, etc. Of course, the corpus data can also be corpus data oriented to general fields or various fields, such as news corpus data (including a large number of standardized terms), social corpus data (including a large number of non-standardized terms), etc. The embodiments of the present disclosure are not limited to these cases. For example, corpus data is a set of a large amount of text data, and for example, each piece of text data usually includes one or a plurality of sentences (which can form one or a plurality of paragraphs).

For example, the corpus data described above may come from a corpus database disclosed by a third party, or may come from a corpus database collected by oneself (for example, collected from the Internet) or a corpus database owned by oneself, or may come from all of them, without being limited in the embodiments of the present disclosure. For example, the computing device can obtain corpus data from a network (for example, a local area network and/or the Internet, etc.), and can also receive corpus data from an input interface (for example, a USB interface). Of course, the corpus data can also be input into the computing device via an input device, such as a keyboard. For example, the computing device can store the corpus data in the memory. It should be noted that although the present disclosure mainly takes that the corpus data is medical text data as an example to illustrate the synonym mining method provided by the embodiments of the present disclosure, it should not be regarded as a limitation to the present disclosure. For example, the medical text data can include electronic medical records, medical literatures, etc.

For example, in some examples, prior to step S100, the synonym mining method described above can further include: performing a pre-process on the corpus data. For example, by cleaning and processing the corpus data through the pre-process, the corpus data can be made to be relatively pure and convenient for further processing, thereby facilitating improving the efficiency and accuracy of the synonym mining method.

For example, in some examples, the pre-process can include: performing an error word correction process on the corpus data to correct error words in the corpus data. For example, in the medical text data, there may be various error words due to input faults, such as "colld" (cold), "vomitting" (vomiting), or the like (the corresponding correct texts are in the brackets). For example, the error word correction process can be performed on the corpus data by using a text error correction module provided by some search platforms, and the error word correction process can also be performed on the corpus data by using a text error correction toolkit built in some text processing software, and the error word correction process can also be manually performed on the corpus data, which is not limited in the embodiments of the present disclosure.

For example, in some examples, the pre-processing can further include: performing a sentence segmentation process on the corpus data to segment the corpus data into a plurality of sentences. For example, in some examples, the corpus data can be segmented into a plurality of sentences according to specific punctuation marks, and the specific punctuation marks include but are not limited to a period, a semicolon, a question mark, an exclamation mark, etc.

It should be noted that in some examples, the pre-process can further include at least one of the processing procedures such as removing garbled characters, removing prohibited words, removing data of invalid format, unifying corpus data into a text format, removing data outside the field (e.g., corpus data of other fields completely irrelevant to the medical field, which is mistakenly entered in the medical text data), etc. For example, the methods and details of the above-mentioned processing procedures can refer to the corresponding common technologies in data pre-processing or data cleaning, which will not be repeated here.

For example, in some examples, based on the plurality of sentences obtained via the sentence segmentation process, one of the machine learning algorithms based on statistics, such as a conditional random field (CRF) model, a maximum entropy Markov model (MEMM), etc., can be adopted to perform the recognition process to obtain a named entity set of at least one category. It should be noted that the method used for named entity recognition (NER) is not limited in the embodiments of the present disclosure, that is, it may not be limited to the methods listed above. For example, in some other examples, a deep learning algorithm (also belonging to the machine learning algorithms based on statistics), such as a long-short term memory (LSTM) network model, a bi-directional long-short term memory (Bi-LSTM) network model, etc., can be adopted to perform the recognition process. For example, in some other examples, the above-mentioned methods can be combined (for example, the CRF model and the Bi-LSTM model can be combined) to perform the recognition process. The embodiments of the present disclosure are not limited to these cases.

For example, in some examples, by performing the recognition process on the corpus data, named entity sets of a plurality of categories can be obtained. For example, in some named entity recognition methods (e.g., the conditional random field model), different named entities can be recognized according to the pre-set part-of-speech tags in the corpus data, and the recognized named entity is classified into a category corresponding to the part-of-speech tag. For example, by performing the recognition process on medical text data, named entity sets of the categories such as disease, drug, medical treatment, etc., can be obtained. For example, with respect to the sentence "Azithromycin can be used to treat bronchitis", the drug entity "azithromycin" belonging to the drug category and the disease entity "bronchitis" belonging to the disease category can be recognized.

For example, in some examples, the named entity set of each category includes a plurality of named entities. Taking the named entity set of the drug category as an example, it may include drug entities, such as "azithromycin" (A-Qi-Mei-Su, in Chinese), "zithromax" (Xi-Shu-Mei, in Chinese), "penicillin" (Qing-Mei-Su, in Chinese), "azido-erythromycin" (A-Qi-Hong-Mei-Su, in Chinese), "erythromycin azide" (Die-Dan-Hong-Mei-Su, in Chinese), "Qing-Kai-Ling," "VC Yinqiao tablet," etc. Due to the existence of the phenomenon that the same entity corresponds to multiple expressions (that is, there exist synonyms), for example, in the named entity set of the drug category mentioned above, "azithromycin" (A-Qi-Mei-Su, in Chinese), "zithromax" (Xi-Shu-Mei, in Chinese), "azido-erythromycin" (A-Qi-Hong-Mei-Su, in Chinese) and "erythromycin azide" (Die-Dan-Hong-Mei-Su, in Chinese), etc., refer to the same drug, and in order to facilitate the automatic understanding and analysis of corpus data, it is usually necessary to normalize multiple expressions corresponding to the same entity (that is, to group named entities with the same semantics into a same cluster) to form a synonym dictionary.

Step S200: performing a clustering process on the plurality of named entities in the named entity set of the each category to obtain a synonym candidate set corresponding to the each category.

For example, in step S200, the clustering process can be performed on the named entity set of at least one category obtained in step S100, so as to obtain one or a plurality of synonym candidate clusters according to the named entity set of each category. Each synonym candidate cluster includes a plurality of named entities, and the plurality of named entities have a relatively high probability (e.g., greater than 0.5, etc.) of being synonymous with each other.

Figure 2:
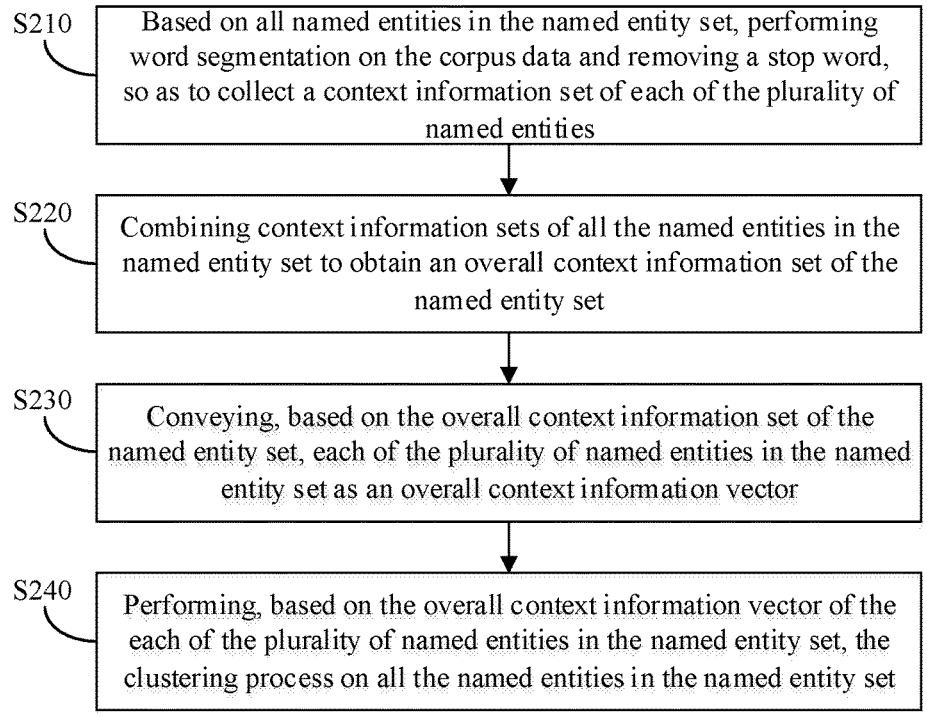
FIG. 2 is an exemplary flowchart corresponding to step S200 illustrated in FIG. 1 and provided by at least one embodiment of the present disclosure.

FIG. 2 is an exemplary flowchart corresponding to step S200 illustrated in FIG. 1 and provided by at least one embodiment of the present disclosure. For example, as illustrated in FIG. 2, the performing the clustering process on the plurality of named entities in the named entity set of the each category to obtain the synonym candidate set corresponding to the each category, that is, step S200, includes steps S210 to S240.

Step S210: based on all named entities in the named entity set, performing word segmentation on the corpus data and removing a stop word, so as to collect a context information set of each of the plurality of named entities.

For example, in some examples, the aforementioned prep-process (specifically, for example, the sentence segmentation process) can be performed on the corpus data to obtain a plurality of sentences, and then word segmentation can be performed on the plurality of sentences which have been obtained, and stop words can be removed.

For example, in some examples, a dictionary-based word segmentation algorithm can be adopted for word segmentation. For example, the dictionary-based word segmentation algorithm includes, but is not limited to, a forward maximum matching method, a reverse maximum matching method, a bi-directional matching word segmentation method, etc. For example, in some other examples, a machine learning algorithm based on statistics can be adopted for word segmentation. For example, the machine learning algorithm based on statistics includes, but is not limited to, hidden Markov model (HMM), MEMM, CRF, support vector machine (SVM), deep learning (including LSTM, Bi-LSTM, etc.), etc. For example, in some other examples, the dictionary-based word segmentation algorithm and the machine learning algorithm based on statistics can be combined (for example, the CRF model and the Bi-LSTM model can be combined) to perform word segmentation. The embodiments of the present disclosure are not limited to these cases. It should be noted that, both named entity recognition and word segmentation are essentially sequence annotations, and they have a high degree of commonality; therefore, in many cases, the named entity recognition and word segmentation can be achieved by basically the same method. For example, in some examples, the word segmentation process in step S210 can be performed at the same time during the recognition process in step S100 described above, without being limited in the embodiments of the present disclosure.

For example, stop words mainly refer to function words which are ubiquitous but usually have no specific meaning in natural language texts. These function words basically do not help natural language processing, but occupy a large amount of storage space, and thus stop words usually need to be removed. For example, stop words in the English text usually include but are not limited to "the," "a," "an," "that," etc., and stop words in the Chinese text usually include but are not limited to "of," "at," "and," "then," "such as," "above-mentioned," etc. For example, in some examples, the stop words among the words obtained via the word segmentation process can be removed according to a stop word list disclosed by a third party, or a custom stop word list, or a combination thereof, without being limited in the embodiments of the present disclosure.

For example, in some examples, after word segmentation is performed on the sentence where a named entity is located and the stop word is removed, part (for example, 1 to 3 words, etc.) or all of the words located before the named entity can be used as the preceding information of the named entity, and part (for example, 1 to 3 words, etc.) or all of the words located after the named entity can be used as the following information of the named entity, so that the context information of the named entity is obtained. It should be noted that in some sentences, the named entity may not possess the preceding information or the following information, and the embodiments of the present disclosure allow such a situation to exist. For example, in some examples, the three words before the named entity and the three words after the named entity are taken as the context information of the named entity. In some cases, after the word segmentation is performed on a certain sentence where the named entity is located and the stop word is removed, exemplarily, if no word is located before the named entity and two words are located after the named entity at the same time, the two words located after the named entity are taken as the context information of the named entity.

Take the sentences "Azido-erythromycin (A-Qi-Hong-Mei-Su, in Chinese) is a semi-synthetic 15-membered macrolide antibiotic" and "Azithromycin (A-Qi-Mei-Su, in Chinese) is the only 15-membered macrolide antibiotic" as examples, the drug entities "azido-erythromycin (A-Qi-Hong-Mei-Su, in Chinese)" and "azithromycin (A-Qi-Mei-Su, in Chinese)" can be recognized through step S100; then, by performing word segmentation on these two sentences and removing the stop words through step S210, the context information set {semi-synthetic, 15-membered macrolide, antibiotic} of the "azido-erythromycin (A-Qi-Hong-Mei-Su, in Chinese)" and the context information set {only, 15-membered macrolide, antibiotic} of the "azithromycin (A-Qi-Mei-Su, in Chinese)" can be collected.

It should be noted that in the embodiments of the present disclosure, a named entity often exists in several sentences. In this case, it is necessary to collect the context information of the named entity based on each of the several sentences and combine all the context information to form the context information set of the named entity. It should be noted that in the process of combining to form the context information set of the named entity, the order of words can be kept unchanged as much as possible, thereby improving the accuracy of subsequent processing. It should be understood that words in the context information set of the named entity are different from each other (similar to the set in mathematics that does not include the same element), that is, a word is incorporated into the context information set of the named entity only when the word appears in the context information of the named entity for the first time, and when the word appears again, the word will not be repeatedly incorporated.

Step S220: combining context information sets of all the named entities in the named entity set to obtain an overall context information set of the named entity set.

For example, in the process of combining to form the overall context information set of the named entity set in Step S220, the order of words can also be kept unchanged as much as possible. For example, in some examples, all the named entities in the named entity set can be randomly sorted, and then the context information sets of all the named entities are combined in turn in a certain order (for example, the order in which each named entity is recognized in step S100 or the order in which the named entities are randomly sorted). In the combining process, a word will be incorporated into the overall context information set of the named entity set only when the word appears in the context information set of one named entity for the first time, and when the word reappears in the context information set of another named entity, the word will not be repeatedly incorporated into the overall context information set of the named entity set.

For example, by step S220, the overall context information set of the named entity set of at least one category can be obtained. For example, the overall context information set of any named entity set is expressed as $\{x_t\}$, where $x_t$ represents the t-th word element (a word element is a word) in the overall context information set of the named entity set, t is an integer, $1 \le t \le T$, and T is the number of word elements in the overall context information set of the named entity set.

Step S230: conveying, based on the overall context information set of the named entity set, each of the plurality of named entities in the named entity set as an overall context information vector.

For example, in some examples, based on the overall context information set $\{x_t\}$ of the named entity set obtained in step S220, the weight $y_t$ of the t-th word element $x_t$ in the set $\{x_t\}$ with respect to each named entity can be calculated, where t takes a value of 1, 2, . . . , and T in turn, so that an overall context information vector $(y_1, y_2, \ldots, y_T)$ of the each named entity can be obtained.

For example, a calculation formula of the weight $y_t$ of the t-th word element $x_t$ with respect to the each named entity is expressed as:

$$y_t = \frac{count(E, x_t)}{count(x_t)},$$

where E represents the each of the plurality of named entities, $count(x_t)$ represents the number of sentences including the t-th word element $x_t$ in the corpus data, and $count(E, x_t)$ represents a count of sentences including both the named entity E and the t-th word element $x_t$ in the corpus data.

It should be understood that the weight $y_t$ of the t-th word element $x_t$ is in the range of [0, 1], where t takes a value of 1, 2, . . . , and T in turn.

Step S240: performing, based on the overall context information vector of the each of the plurality of named entities in the named entity set, the clustering process on all the named entities in the named entity set.

For example, in some examples, step S240 can include: taking each of the plurality of named entities in the named entity set as a candidate cluster, and taking the overall context information vector of the each of the plurality of named entities as a center vector of a corresponding candidate cluster; and performing the clustering process on all current candidate clusters until all the current candidate clusters cannot continue to be clustered.

Figure 3:
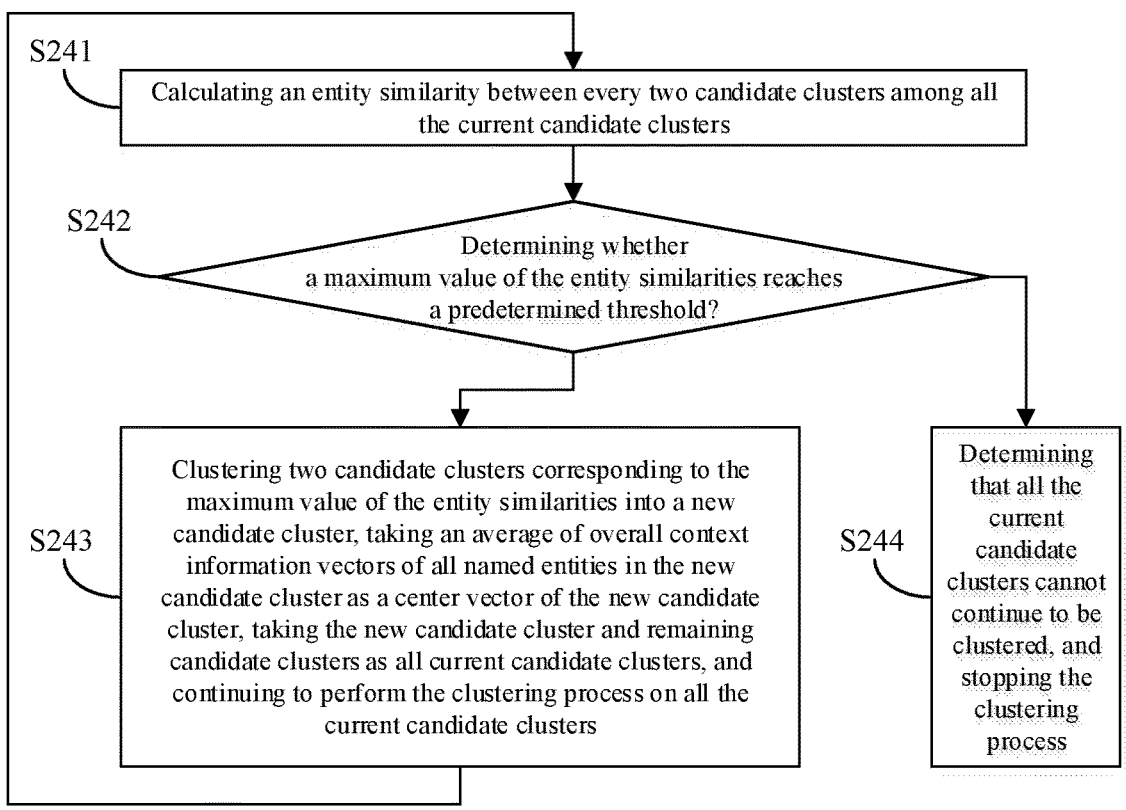
FIG. 3 is a flowchart of a clustering processing method provided by at least one embodiment of the present disclosure.

FIG. 3 is a flowchart of a clustering processing method provided by at least one embodiment of the present disclosure. As illustrated in FIG. 3, the performing the clustering process on all the current candidate clusters can include steps S241 to S244.

Step S241: calculating an entity similarity between every two candidate clusters among all the current candidate clusters.

Step S242: determining whether a maximum value of the entity similarities reaches a predetermined threshold, if the maximum value of the entity similarity reaches the predetermined threshold, performing the following step S243, and if the maximum value of the entity similarity does not reach the predetermined threshold, performing the following step S244.

Step S243: clustering two candidate clusters corresponding to the maximum value of the entity similarities into a new candidate cluster, taking an average of overall context information vectors of all named entities in the new candidate cluster as a center vector of the new candidate cluster, taking the new candidate cluster and remaining candidate clusters as all current candidate clusters, and continuing to perform the clustering process on all the current candidate clusters.

Step S244: determining that all the current candidate clusters cannot continue to be clustered, and stopping the clustering process.

For example, in some examples, in step S241, the entity similarity between any two candidate clusters can be calculated based on the center vectors of the any two candidate clusters. For example, a calculation formula of the entity similarity between any two candidate clusters can be expressed as:

$$Sim(F_1, F_2) = \frac{V(F_1) \cdot V(F_2)}{|V(F_1)| \times |V(F_2)|},$$

where $V(F_1)$ and $V(F_2)$ represent center vectors of the any two candidate clusters, respectively, $V(F_1) \cdot V(F_2)$ represents a dot product of the center vectors $V(F_1)$ and $V(F_2)$ of the any two candidate clusters, and $|V(F_1)|$ and $|V(F_2)|$ represent modulus of the center vectors $V(F_1)$ and $V(F_2)$ of the any two candidate clusters, respectively.

It should be understood that the entity similarity of any two candidate clusters is in the range of [0, 1]. For example, the closer the entity similarity is to 1, the smaller the difference between the contexts applicable to the named entities in the two candidate clusters, and therefore, it is more likely that the named entities in the two candidate clusters are synonymous with each other. On the contrary, the closer the entity similarity is to 0, the greater the difference between the contexts applicable to the named entities in the two candidate clusters, and therefore, it is more likely that that the named entities in the two candidate clusters are not synonymous with each other.

For example, in some examples, in step S242, the maximum value of the (plurality of) entity similarities can be determined according to the (plurality of) entity similarities obtained in step S241, and then according to the magnitude comparison relationship between the maximum value and the predetermined threshold, it is determined whether to perform step S243 or to perform step S244 subsequently.

For example, in the embodiments of the present disclosure, the predetermined threshold can be appropriately set according to needs. For example, if the predetermined threshold is set to be relatively large, the named entities clustered into the same candidate cluster are more likely to be synonyms. However, it should be noted that in this case, it is also likely to exclude a named entity (belonging to the synonyms of the candidate cluster) that should have been clustered into the same candidate cluster, that is, there is a problem of incomplete clustering. For example, if the predetermined threshold is set to be relatively small, the problem of incomplete clustering can be avoided to a great extent. However, it should be noted that in this case, it is likely to cluster, a named entity (i.e., noise) that does not originally belong to the same candidate cluster, into the same candidate cluster, that is, there is a problem of inaccurate clustering. For example, in some examples, in order to take into account both aspects of clustering problems (that is, the problem of incomplete clustering and the problem of inaccurate clustering), the predetermined threshold can be set to be 0.70.9, such as 0.7, 0.75, 0.8, 0.85, 0.9, etc., without being limited in the embodiments of the present disclosure.

For example, in some examples, in the current (plurality of) candidate clusters obtained after step S243 is performed, there may be cases where named entities in some candidate clusters are synonymous with each other, and thus it is necessary to continue performing the clustering process thereon, that is, the processing of the aforementioned step S241 and the processing of the aforementioned step S242 are repeated.

For example, in some examples, after the clustering process is performed for a plurality of times, if the maximum value of the entity similarities obtained in step S242 does not reach the predetermined threshold, it indicates that according to the pre-set judgment standard (i.e., the predetermined threshold), there is no case in which named entities in any two candidate clusters are synonymous with each other in the current candidate clusters, and thus, the clustering process can be stopped.

It should be understood that in the above description of step S240, each named entity in the named entity set is taken as one candidate cluster, and the overall context information vector of each named entity is taken as the center vector of the corresponding candidate cluster, so that it is convenient to illustrate the clustering processing method presented in step S241 to step S244. Those skilled in the art should understand that the above operations serve as an aid for illustration, and should not be regarded as a limitation to the present disclosure.

For example, after the clustering process in step S200, for the named entity set of each category, a plurality of synonym candidate clusters can usually be obtained (for example, the candidate cluster obtained after step S244 is performed can be defined as a synonym candidate cluster), and the plurality of synonym candidate clusters form a corresponding synonym candidate set. It should be noted that noise may still exist in the above-mentioned synonym candidate cluster, that is, there may be one or several named entities which are semantically different from the remaining named entities among the plurality of named entities in one synonym candidate cluster. Therefore, it is usually necessary to perform noise filtering on each synonym candidate cluster in the synonym candidate set, so as to remove possible noise and improve the purity of each synonym candidate cluster.

Step S300: performing, based on a word form similarity and a context similarity, a filtering process on the synonym candidate set corresponding to the each category to obtain a synonym set corresponding to the each category.

For example, in step S300, the plurality of named entities in each synonym candidate cluster can be filtered based on the word form similarity and the context similarity, so as to remove possible noise and improve the purity of each synonym candidate cluster.

Figure 4:
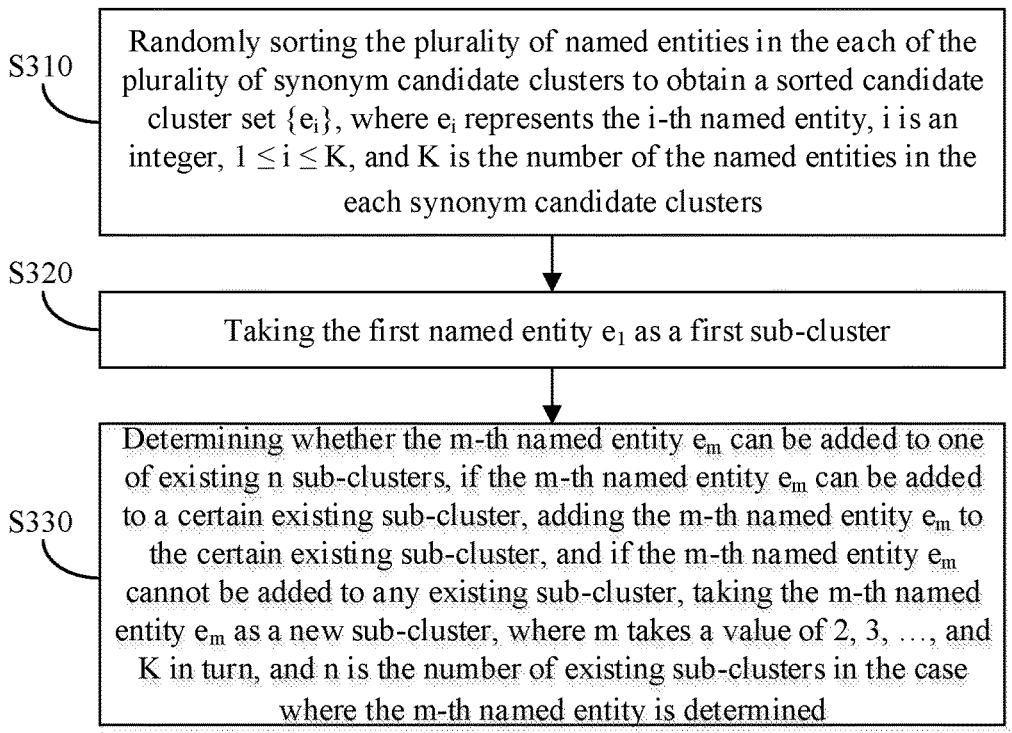
FIG. 4 is a flowchart of a filtering processing method provided by at least one embodiment of the present disclosure.

FIG. 4 is a flowchart of a filtering processing method provided by at least one embodiment of the present disclosure. As illustrated in FIG. 4, the performing the filtering process on the plurality of named entities in the each synonym candidate cluster can include steps S310 to S330.

Step S310: randomly sorting the plurality of named entities in the each of the plurality of synonym candidate clusters to obtain a sorted candidate cluster set $\{e_i\}$, where $e_i$ represents the i-th named entity, i is an integer, $1 \leq i \leq K$, and K is the number of the named entities in the each synonym candidate clusters;

Step S320: taking the first named entity $e_i$ as a first sub-cluster;

Step S330: determining whether the m-th named entity $e_m$ can be added to one of existing n sub-clusters, if the m-th named entity $e_m$ can be added to a certain existing sub-cluster, adding the m-th named entity $e_m$ to the certain existing sub-cluster, and if the m-th named entity $e_m$ cannot be added to any existing sub-cluster, taking the m-th named entity $e_m$ as a new sub-cluster, where m takes a value of 2, 3, . . . , and K in turn, and n is the number of existing sub-clusters in the case where the m-th named entity is determined.

It should be understood that when filtering the plurality of named entities in each synonym candidate cluster, the problem actually needs to be solved is still a clustering problem, that is, clustering the plurality of named entities in the synonym candidate cluster, so as to distinguish real synonyms from noise. Usually, after the above-mentioned filtering process, one or a plurality of large sub-clusters (for example, a large sub-cluster includes two or more named entities) and one or a plurality of small sub-clusters (for example, a small sub-cluster includes only one named entity corresponding to noise) can be obtained based on one synonym candidate cluster. For example, one synonym candidate cluster usually corresponds to one large sub-cluster, and the embodiments of the present disclosure include but are not limited to this case. For example, the large sub-clusters corresponding to each synonym candidate cluster in the named entity set of each category can form the synonym set corresponding to the named entity set of the each category.

For example, in some examples, in step S330, the determining whether the m-th named entity $e_m$ can be added to one of the existing n sub-clusters can include: determining whether the m-th named entity $e_m$ can be added to an existing j-th sub-cluster, where j takes a value of 1, 2, . . . , and n in turn. For example, in some examples, specifically, the determining whether the m-th named entity $e_m$ can be added to the existing j-th sub-cluster can include: calculating a word form similarity and a context similarity between the m-th named entity $e_m$ and each named entity in the existing j-th sub-cluster, wherein if a proportion of named entities, which satisfy a predetermined relationship with the m-th named entity $e_m$ in terms of the word form similarity and the context similarity, in the existing j-th sub-cluster, reaches a predetermined proportion threshold, the m-th named entity $e_m$ can be added to the j-th sub-cluster, or else, the m-th named entity $e_m$ cannot be added to the j-th sub-cluster.

For example, in some examples, the word form similarity between any two named entities $e_a$ and $e_b$ can be calculated based on the minimum edit distance. For example, the minimum edit distance refers to the minimum number of editing operations required for two character strings to be converted from one to the other. For example, permitted editing operations include replacing one character with another character, inserting one character, deleting one character, etc. For example, in the embodiments of the present disclosure, it can be defined that the edit distance value corresponding to one editing operation performed on one character string is 1, and when one character string is converted to another character string, the sum of edit distance values of all edit operations is calculated, and the sum is the minimum edit distance between the two character strings. For example, in the embodiments of the present disclosure, each named entity corresponds to one character string, and each word (for example, a word can be a Chinese character or an English letter, etc.) in the named entity corresponds to a character. For example, illustratively, the minimum edit distance between "A-Qi-Mei-Su" and "A-Qi-Hong-Mei-Su" is 1, because "A-Qi-Mei-Su" can be obtained by simply deleting the Chinese character "Hong" in "A-Qi-Hong-Mei-Su"; and the minimum edit distance between "A-Qi-Mei-Su" and "Xi-Shu-Mei" is 4.

For example, the word form similarity between the any two named entities $e_a$ and $e_b$ can be calculated according to the following formula:

$$S_1(e_a, e_b) = 1 - \frac{dis(e_a, e_b)}{\max(len(e_a), len(e_b))},$$

where $S_1(e_a, e_b)$ represents the word form similarity, $dis(e_a, e_b)$ represents a minimum edit distance between the two named entities $e_a$ and $e_b$, $len(e_a)$ represents a word length of the named entity $e_a$, $len(e_b)$ represents a word length of the named entity $e_b$, and $\max(len(e_a), len(e_b))$ represents a maximum of $len(e_a)$ and $len(e_b)$.

It should be understood that the word form similarity described above is in the range of [0, 1].

It should be understood that the use of word form similarity as a judgment basis is helpful to find synonyms with small difference in word form, such as the "A-Qi-Mei-Su" and "A-Qi-Hong-Mei-Su" listed above (the word form similarity is 4/5), and is not helpful to find synonyms with large difference in word form, such as "A-Qi-Mei-Su" and "Xi-Shu-Mei" listed above (the word form similarity is 0). Therefore, in the embodiments of the present disclosure, in addition to the word form similarity, the context similarity is also introduced as a judgment basis in the filtering process described above.

For example, in some examples, the context similarity between the any two named entities $e_a$ and $e_b$ can be calculated according to the following formula:

$$S_2(e_a, e_b) = \frac{p(e_b|e_a) + p(e_a|e_b)}{2},$$

where $S_2(e_a, e_b)$ represents the context similarity, $p(e_b|e_a)$ represents a probability of generating the named entity $e_b$ form the named entity $e_a$, and $p(e_a|e_b)$ represents a probability of generating the named entity $e_a$ from the named entity $e_b$.

For example, in some examples, $p(e_b|e_a)$ and $p(e_a|e_b)$ can be calculated according to the following formulas:

$$p(e_b|e_a) = \sum_{u \in C(e_a)} p(u|e_a)p(e_b|u),$$

$$p(e_a|e_b) = \sum_{v \in C(e_b)} p(v|e_b)p(e_a|v),$$

where $C(e_a)$ represents a context information set of the named entity $e_a$, u represents a word element in $C(e_a)$, $p(u|e_a)$ represents a probability of generating the word element u from the named entity $e_a$, $p(e_b|u)$ represents a probability of generating the named entity $e_b$ from the word element u, $C(e_b)$ represents a context information set of the named entity $e_b$, v represents a word element in $C(e_b)$, $p(v|e_b)$ represents a probability of generating the word element v from the named entity $e_b$, and $p(e_a|v)$ represents a probability of generating the named entity $e_a$ from the word element v.

For example, $p(u|e_a)$, $p(e_b|u)$, $p(v|e_b)$ and $p(e_a|v)$ can be calculated by using the maximum likelihood method. For example, the calculation formulas are as follows:

$$p(u|e_a) = \frac{count(u, e_a)}{count(e_a)},$$

$$p(e_b|u) = \frac{count(e_b, u)}{count(u)},$$

$$p(v|e_b) = \frac{count(v, e_b)}{count(e_b)},$$

$$p(e_a|v) = \frac{count(e_a, v)}{count(v)},$$

where $count(e_a)$ represents a count of sentences including the named entity $e_a$ in the corpus data, $count(e_b)$ represents a count of sentences including the named entity $e_b$ in the corpus data, $count(u)$ represents a count of sentences including the word element u in the corpus data, $count(v)$ represents a count of sentences including the word element v in the corpus data, $count(u, e_a)$ represents a count of sentences including both the word element u and the named entity $e_a$ in the corpus data, $count(e_b, u)$ represents a count of sentences including both the named entity $e_b$ and the word element u in the corpus data, $count(v, e_b)$ represents a count of sentences including both the word element v and the named entity $e_b$ in the corpus data, and $count(e_a, v)$ represents a count of sentences including both the named entity $e_a$ and the word element v in the corpus data It should be understood that the context similarity described above is in the range of [0, 1]. It should be understood that the use of context similarity as a judgment basis is helpful to find synonyms with large difference in word form and small difference in context, such as "A-Qi-Mei-Su" and "Xi-Shu-Mei" listed above. The word form similarity therebetween is 0, but they refer to the same drug, so the difference in context is small. And therefore, when the context similarity is used as a judgment basis, it can usually be determined that "A-Qi-Mei-Su" and "Xi-Shu-Mei" are synonymous with each other.

For example, after the word form similarity and the context similarity between the any two named entities $e_a$ and $e_b$ are calculated, it can be determined whether $e_a$ and $e_b$ satisfy the predetermined relationship as follows:

$$(S_1(e_a,e_b))^2+(S_2(e_a,e_b))^2 \geq 1$$

where $S_1(e_a, e_b)$ represents the word form similarity between the any two named entities $e_a$ and $e_b$, and $S_2(e_a, e_b)$ represents the context similarity between the any two named entities $e_a$ and $e_b$. For example, if the above-mentioned predetermined relationship is satisfied (that is, the above-mentioned inequality holds), the named entities $e_a$ and $e_b$ are synonyms; otherwise, the named entities $e_a$ and $e_b$ are not synonyms.

For example, in the embodiments of the present disclosure, the predetermined proportion threshold can be appropriately set according to needs. For example, if the predetermined proportion threshold is set to be relatively large, there may be a problem of excessive filtering, that is, the problem of filtering out real synonyms. For example, if the predetermined proportion threshold is set to be relatively small, there may be a problem of insufficient filtering, that is, the problem of not filtering out the noise. For example, the predetermined proportion threshold can be set to be 70%-90%, such as 70%, 75%, 80%, 85%, 90%, etc.

For example, in the embodiments of the present disclosure, the basis of determining the synonyms in the filtering process combines the word form similarity and the context similarity, and therefore, it is beneficial to improve the accuracy and precision of synonym mining.

For example, after the filtering process in step S300, at least part of the noise is removed, so the obtained synonym set can have a higher purity. At the same time, each cluster in the synonym set represents a group of synonyms (two or more synonyms).

Step S400: constructing a synonym dictionary based on the synonym set corresponding to the each category.

For example, in some examples, a synonym dictionary can be constructed based on the synonym set(s) corresponding to the named entity set of each category and obtained in step S300. For example, the synonym dictionary can be constructed in a way that is convenient for retrieval. For example, in some examples, the synonym sets can be arranged according to the frequency of use of each synonym set, and at the same time, the named entities in each synonym set can be arranged according to the frequency of use of the named entities in the each synonym set, which is not limited in the embodiments of the present disclosure.

For example, the constructed synonym set can be stored on a computer-readable storage medium, so that the constructed synonym set can be copied and transmitted via the computer-readable storage medium. For another example, the constructed synonym set can be stored in a cloud (including public cloud or private cloud) storage space, so that the constructed synonym set can be copied and transmitted via the Internet. The embodiments of the present disclosure are not limited to these cases.

For example, in some examples, via the foregoing steps S100 to S400, a medical synonym dictionary can be constructed based on medical text data, and the medical synonym dictionary can be used for tasks such as automatic analysis and understanding of medical texts, retrieval, etc.

It should be noted that, in the embodiments of the present disclosure, the operations of the foregoing steps can be executed by means of software, hardware, firmware, or any combination thereof, so that corresponding processing procedures can be implemented respectively.

It should be noted that, in the embodiments of the present disclosure, the flow of the above-mentioned synonym mining method can include more or fewer operations, and these operations may be executed sequentially or in parallel. Although the flow of the synonym mining method described above includes a plurality of operations appearing in a specific order, it should be clearly understood that the order of the plurality of operations is not limited. The synonym mining method described above can be executed once or multiple times according to predetermined conditions.

The synonym mining method provided by the embodiments of the present disclosure can filter, based on the word form similarity and the context similarity, the synonym candidate set obtained by the clustering process, thereby improving the purity of the obtained synonym set, and further, a synonym dictionary can be constructed based on the obtained synonym set, so that the accuracy of knowledge filtering tasks, keyword extraction tasks, text classification tasks, semantic clustering tasks, or the like can be improved in the case where the synonym dictionary is applied to the natural language processing field.

Figure 5A:
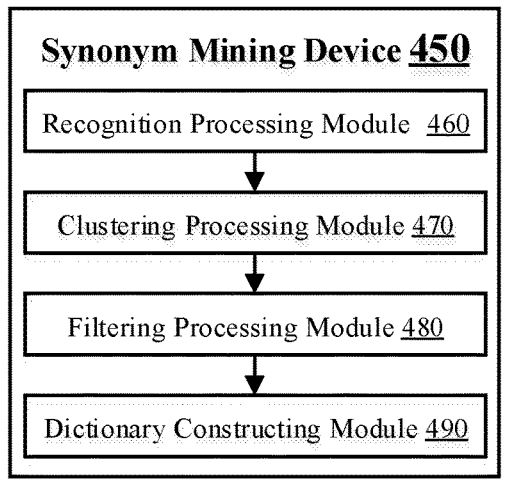
FIG. 5A is a schematic block diagram of a synonym mining device provided by at least one embodiment of the present disclosure.

At least one embodiment of the present disclosure further provides a synonym mining device. FIG. 5A is a schematic block diagram of a synonym mining device provided by at least one embodiment of the present disclosure. For example, as illustrated in FIG. 5A, the synonym mining device 450 includes a recognition processing module 460, a clustering processing module 470, and a filtering processing module 480.

For example, the recognition processing module 460 is configured to perform a recognition process on corpus data to obtain a named entity set of at least one category. That is to say, the recognition processing module 460 can be used to execute step S100 in the aforementioned synonym mining method. For example, the procedure and details of the recognition process performed by the recognition processing module 460 can refer to the related description of the foregoing step S100, without being repeated here.

For example, the clustering processing module 470 is configured to perform a clustering process on the named entity set of the each category to obtain a synonym candidate set corresponding to the each category. That is to say, the clustering processing module 470 can be used to execute step S200 in the aforementioned synonym mining method. For example, the procedure and details of the clustering process performed by the clustering processing module 470 can refer to the related description of the foregoing step S200, without being repeated here.

For example, the filtering processing module 480 is configured to perform, based on a word form similarity and a context similarity, a filtering process on the synonym candidate set corresponding to the each category to obtain a synonym set corresponding to the each category. That is to say, the filtering processing module 480 can be used to execute step S300 in the aforementioned synonym mining method. For example, the procedure and details of the filtering process performed by the filtering processing module 480 can refer to the related description of the foregoing step S300, without being repeated here.

For example, in some embodiments, as illustrated in FIG. 5A, the synonym mining device 450 can further include a dictionary constructing module 490. For example, the dictionary constructing module 490 is configured to construct a synonym dictionary based on the synonym set corresponding to the each category. That is to say, the dictionary constructing module 490 can be used to execute step S400 in the aforementioned synonym mining method. For example, the procedure and details of the dictionary constructing process performed by the dictionary constructing module 490 can refer to the related description of the foregoing step S400, without being repeated here.

It should be noted that the recognition processing module 460, the clustering processing module 470, the filtering processing module 480, and the dictionary constructing module 490 in the synonym mining device 450 can all be implemented as hardware, software, firmware, or any combination thereof. It should be understood that the synonym mining device 450 can be used to execute the synonym mining method provided by any one of the embodiments of the present disclosure.

Figure 5B:
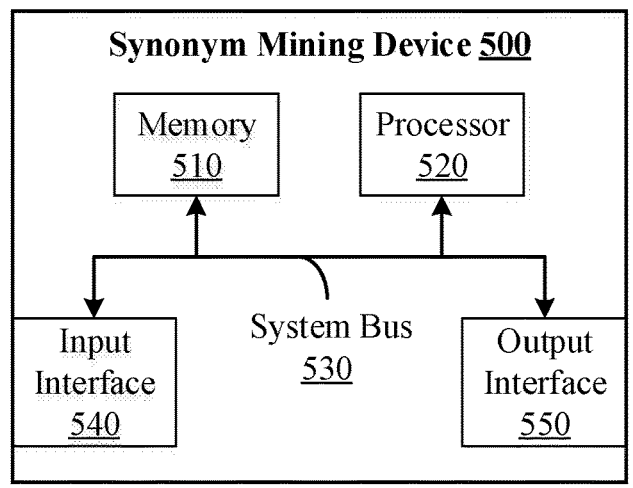
FIG. 5B is a schematic block diagram of another synonym mining device provided by at least one embodiment of the present disclosure.

FIG. 5B is a schematic block diagram of another synonym mining device provided by at least one embodiment of the present disclosure. For example, as illustrated in FIG. 5B, the synonym mining device 500 includes a memory 510 and a processor 520. For example, the memory 510 is configured to store computer readable instructions non-transitorily, and the processor 520 is configured to execute the computer readable instructions. Upon the computer readable instructions being executed by the processor 520, the synonym mining method provided by any one of the embodiments of the present disclosure is executed.

For example, the memory 510 and the processor 520 can communicate with each other directly or indirectly. For example, in some examples, as illustrated in FIG. 5B, the synonym mining device 500 can further include a system bus 530, and the memory 510 and the processor 520 can communicate with each other through the system bus 530. For instance, the processor 520 can access the memory 510 through the system bus 530. For instance, in some other examples, components such as the memory 510 and the processor 520 can communicate with each other via network connection. The network can include a wireless network, a wired network, and/or any combination of the wireless network and the wired network. The network can include local area network (LAN), the Internet, a telecommunication network, Internet of Things based on the Internet and/or the telecommunication network, and/or any combination of the above networks, etc. The wired network, for example, can communicate by means of twisted pair, coaxial cable or optical fiber transmission, etc. The wireless network, for example, can adopt a communication mode such as 3G/4G/5G mobile communication network, Bluetooth, Zigbee or WiFi, etc. The present disclosure does not limit the type and function of the network.

For example, the processor 520 can control other components in the synonym mining device to realize desired functions. The processor 520 can be an element having synonym mining capability and/or program execution capability, such as a central processing unit (CPU), a tensor processing unit (TPU), or a graphics processing unit (GPU). The CPU can have an X86 or ARM architecture, etc. The GPU can be integrated directly on the motherboard alone or built into the Northbridge chip of the motherboard. The GPU can also be built into the CPU.

For example, the memory 510 can include one or a plurality of computer program products, and the computer programs can include a computer readable storage medium of diverse forms, such as a volatile memory and/or a non-volatile memory. The volatile memory, for instance, can include a random access memory (RAM) and/or a cache, etc. The non-volatile memory, for example, can include a read-only memory (ROM), a hard disk, an erasable programmable read-only memory (EPROM), a portable compact disk read-only memory (CD-ROM), a USB memory, or a flash memory, etc.

For example, one or a plurality of computer instructions can be stored on the memory 510, and the processor 520 can execute the computer instructions to realize various functions. The computer readable storage medium can also store various applications and various data, such as the overall context information vector of each named entity, the word form similarity, the context similarity, and various data used and/or generated by the application programs, etc.

For example, when some computer instructions stored on the memory 510 are executed by the processor 520, one or more steps in the synonym mining method described above can be executed. For example, when some other computer instructions stored on the memory 510 are executed by the processor 520, the synonym dictionary obtained by the above synonym mining method can be used to perform any tasks in the natural language processing field, such as a knowledge filtering task, a keyword extraction task, a text classification task, a semantic clustering task, etc.

For example, as illustrated in FIG. 5B, the synonym mining device 500 can further include an input interface 540 that allows an external device to communicate with the synonym mining device 500. For example, the input interface 540 can be configured to receive instructions from an external computer device and a user, etc. The synonym mining device 500 can further include an output interface 550 that allows the synonym mining device 500 to be connected with one or more external devices. For example, the synonym mining device 500 can display images and the like through the output interface 550. The external devices that communicate with the synonym mining device 500 through the input interface 540 and/or the output interface 550 can be included in an environment that provides a user interface of any type with which the user can interact with the external devices. Examples of the types of user interfaces include graphical user interface (GUI), natural user interface, etc. For example, the GUI can receive an input from a user via an input device such as a keyboard, a mouse, a remote controller, and the like, and provide an output on an output device such as a display. In addition, the natural user interface can enable a user to interact with the synonym mining device 500 in a manner that is not constrained by input devices such as keyboards, mice and remote controllers, etc. In contrast, the natural user interface can rely on voice recognition, touch and stylus recognition, gesture recognition on and near the screen, aerial gesture, head and eye tracking, speech and semantics, vision, touch, gesture, and machine intelligence, etc.

In addition, although the synonym mining device 450 and the synonym mining device 500 are shown as an individual terminal/system in FIG. 5A and FIG. 5B, it should be understood that the synonym mining device 450 and the synonym mining device 500 can also be a distributed terminal/system, and can also be deployed as a cloud facility (including public cloud or private cloud). Thus, for example, a plurality of devices can communicate with each other via network connection and execute the tasks that are described to be executed by the synonym mining device 450 or the synonym mining device 500 together. For example, in some embodiments, the corpus data can be obtained through a client terminal and the corpus data can be uploaded to a server through the network; after the server executes the procedure of the synonym mining method, the mining result (for example, a synonym set, a synonym dictionary, or the like) can be returned to the client terminal through the network. For example, in some embodiments, the executing procedure of the synonym mining method can be implemented on the terminal. For example, the executing procedure of the synonym mining method can be implemented partly on the terminal and partly on the server.

For example, detailed description of the processing procedure of the synonym mining method can refer to the relevant description of the synonym mining method in the above embodiments, and no further description will be given here.

It should be noted that the synonym mining device provided by the embodiments of the present disclosure is illustrative but not limitative, and the synonym mining device can also include other conventional components or structures according to actual application requirements. For example, in order to implement necessary functions of the synonym mining device, those skilled in the art can set other conventional components or structures according to specific application scenarios, which are not limited in the embodiments of the present disclosure.

The technical effects of the synonym mining device provided by the embodiments of the present disclosure can be referred to the related description of the synonym mining method in the foregoing embodiments, and no further description will be given here.

Figure 6:
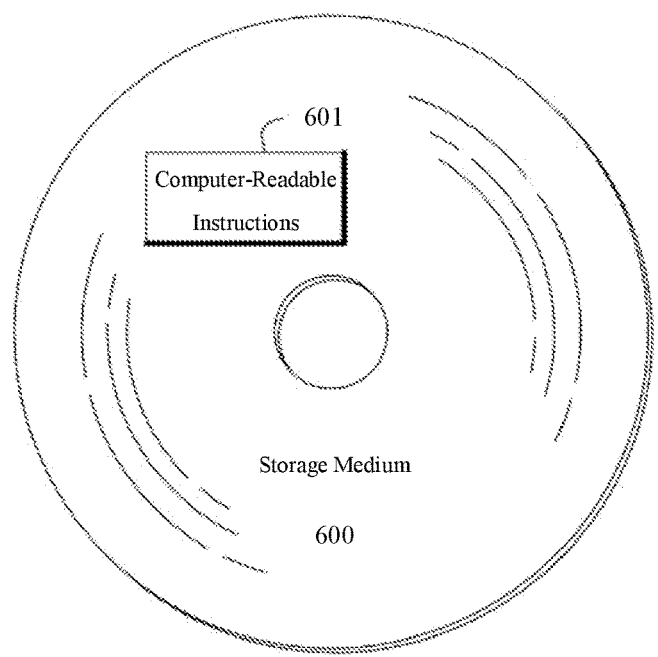
FIG. 6 is a schematic diagram of a storage medium provided by at least one embodiment of the present disclosure.

At least one embodiment of the present disclosure further provides a storage medium. FIG. 6 is a schematic diagram of a storage medium provided by one embodiment of the present disclosure. For example, as illustrated in FIG. 6, the storage medium 600 is configured to store computer readable instructions 601 non-transitorily. Upon the non-transitory computer readable instructions 601 being executed by a computer (including a processor), instructions of the synonym mining method provided by any one of the embodiments of the present disclosure can be executed.

For example, one or more computer instructions can be stored on the storage medium 600. Some computer instructions stored on the storage medium 600 can be, for instance, instructions for implementing one or more steps in the above-mentioned synonym mining method.

For example, the storage medium can include a storage component of a tablet, a hard disk of a personal computer, a random access memory (RAM), a read-only memory (ROM), an erasable programmable read-only memory (EPROM), a portable compact disk read-only memory (CD-ROM), a flash memory, or any combination of the above-mentioned storage media, or other suitable storage medium.

The technical effects of the storage medium provided by the embodiments of the present disclosure can refer to the related description of the synonym mining method in the foregoing embodiments, and no further description will be given here.

For the disclosure, the following statements should be noted:

(1) The accompanying drawings related to the embodiment(s) of the present disclosure involve only the structure(s) in connection with the embodiment(s) of the present disclosure, and other structure(s) can be referred to common design(s).

(2) In case of no conflict, features in one embodiment or in different embodiments of the present disclosure can be combined.

What have been described above are only specific implementations of the present disclosure, and the protection scope of the present disclosure is not limited thereto. Any changes or substitutions easily occur to those skilled in the art within the technical scope of the present disclosure should be covered in the protection scope of the present disclosure. Therefore, the protection scope of the present disclosure should be determined based on the protection scope of the claims.

What is claimed is:

1. A synonym mining method, comprising:
performing a recognition process on corpus data to obtain a named entity set of at least one category, wherein the named entity set of each category comprises a plurality of named entities;
performing a clustering process on the plurality of named entities in the named entity set of the each category to obtain a synonym candidate set corresponding to the each category; and
performing, based on a word morphology similarity and a context similarity, a filtering process on the synonym candidate set corresponding to the each category to obtain a synonym set corresponding to the each category;
wherein the synonym candidate set comprises a plurality of synonym candidate clusters, and each of the plurality of synonym candidate clusters comprises a plurality of named entities; and
the performing the filtering process on the synonym candidate set comprises:
performing the filtering process on the plurality of named entities in each of the plurality of synonym candidate clusters; and
wherein the performing the filtering process on the plurality of named entities in the each of the plurality of synonym candidate clusters comprises:
randomly sorting the plurality of named entities in the each of the plurality of synonym candidate clusters to obtain a sorted candidate cluster set $\{e_i\}$, where $e_i$ represents an i-th named entity, i is an integer, $1 \leq i \leq K$, and K is a count of the named entities in the each of the plurality of synonym candidate clusters;
taking a first named entity $e_i$ as a first sub-cluster; and
determining whether an m-th named entity $e_m$ can be added to one of existing n sub-clusters,
if the m-th named entity $e_m$ can be added to a certain existing sub-cluster, adding the m-th named entity $e_m$ to the certain existing sub-cluster, and
if the m-th named entity $e_m$ cannot be added to any existing sub-cluster, taking the m-th named entity $e_m$ as a new sub-cluster,
where m takes a value of 2, 3, . . . , and K in turn, and n is a count of existing sub-clusters in a case where the m-th named entity is determined.

2. The synonym mining method according to claim 1, wherein the determining whether the m-th named entity $e_m$ can be added to one of the existing n sub-clusters comprises:
determining whether the m-th named entity $e_m$ can be added to an existing j-th sub-cluster, where j takes a value of 1, 2, . . . , and n in turn; and
the determining whether the m-th named entity $e_m$ can be added to the existing j-th sub-cluster comprises:
calculating a word morphology similarity and a context similarity between the m-th named entity $e_m$ and each named entity in the existing j-th sub-cluster,
wherein if a proportion of named entities, which satisfy a predetermined relationship with the m-th named entity $e_m$ in terms of the word morphology similarity and the context similarity, in the existing j-th sub-cluster, reaches a predetermined proportion threshold, the m-th named entity $e_m$ can be added to the j-th sub-cluster, or else, the m-th named entity $e_m$ cannot be added to the j-th sub-cluster.

3. The synonym mining method according to claim 2, wherein the predetermined relationship is expressed as:

$$(S_1(e_a,e_b))^2+(S_2(e_a,e_b))^2 \geq 1$$

where $S_1(e_a, e_b)$ represents a word morphology similarity between any two named entities $e_a$ and $e_b$, and $S_2(e_a, e_b)$ represents a context similarity between the any two named entities $e_a$ and $e_b$.

4. The synonym mining method according to claim 3, wherein the word morphology similarity between the any two named entities $e_a$ and $e_b$ is expressed as:

$$S_1(e_a, e_b) = 1 - \frac{dis(e_a, e_b)}{\max(len(e_a), len(e_b))},$$

where $S_1(e_a, e_b)$ represents the word morphology similarity, $dis(e_a, e_b)$ represents a minimum edit distance between the two named entities $e_a$ and $e_b$, $len(e_a)$ represents a word length of the named entity $e_a$, $len(e_b)$ represents a word length of the named entity $e_b$, and $\max(len(e_a), len(e_b))$ represents a maximum of $len(e_a)$ and $len(e_b)$.

5. The synonym mining method according to claim 4, wherein the context similarity between the any two named entities $e_a$ and $e_b$ is expressed as:

$$S_2(e_a,e_b) = \frac{p(e_b|e_a) + p(e_a|e_b)}{2},$$

where $S_2(e_a, e_b)$ represents the context similarity, $p(e_b|e_a)$ represents a probability of generating the named entity $e_b$ form the named entity $e_a$, and $p(e_b|e_a)$ represents a probability of generating the named entity $e_a$ from the named entity $e_b$.

6. The synonym mining method according to claim 5, wherein the probability $p(e_b|e_a)$ of generating the named entity $e_b$ form the named entity $e_a$ and the probability $p(e_b|e_a)$ of generating the named entity $e_a$ from the named entity $e_b$ are respectively expressed as:

$$p(e_b|e_a) = \sum_{u \in C(e_a)} p(u|e_a)p(e_b|u),$$

$$p(e_a|e_b) = \sum_{v \in C(e_b)} p(v|e_b)p(e_a|v),$$

where $C(e_a)$ represents a context information set of the named entity $e_a$, u represents a word element in $C(e_a)$, $p(u|e_a)$ represents a probability of generating the word element u from the named entity $e_a$, $p(e_b|u)$ represents a probability of generating the named entity $e_b$ from the word element u, $C(e_b)$ represents a context information set of the named entity $e_b$, v represents a word element in $C(e_b)$, $p(v|e_b)$ represents a probability of generating the word element v from the named entity $e_b$, and $p(e_a|v)$ represents a probability of generating the named entity $e_a$ from the word element v.

7. The synonym mining method according to claim 6, wherein the probability $p(u|e_a)$ of generating the word element u from the named entity $e_a$, the probability $p(e_b|u)$ of generating the named entity $e_b$ from the word element u, the probability $p(v|e_b)$ of generating the word element v from the named entity $e_b$, and the probability $p(e_a|v)$ of generating the named entity $e_a$ from the word element v are respectively expressed as:

$$p(u|e_a) = \frac{count(u, e_a)}{count(e_a)},$$

$$p(e_b|u) = \frac{count(e_b, u)}{count(u)},$$

$$p(v|e_b) = \frac{count(v, e_b)}{count(e_b)},$$

$$p(e_a|v) = \frac{count(e_a, v)}{count(v)},$$

where $count(e_a)$ represents a count of sentences comprising the named entity $e_a$ in the corpus data, $count(e_b)$ represents a count of sentences comprising the named entity $e_b$ in the corpus data, count(u) represents a count of sentences comprising the word element u in the corpus data, count(v) represents a count of sentences comprising the word element v in the corpus data, $count(u, e_a)$ represents a count of sentences comprising both the word element u and the named entity $e_a$ in the corpus data, $count(e_b, u)$ represents a count of sentences comprising both the named entity $e_b$ and the word element u in the corpus data, $count(v, e_b)$ represents a count of sentences comprising both the word element v and the named entity eb in the corpus data, and $count(e_a, v)$ represents a count of sentences comprising both the named entity $e_a$ and the word element v in the corpus data.

8. The synonym mining method according to claim 1, wherein the performing the clustering process on the plurality of named entities in the named entity set of the each category comprises:

based on all named entities in the named entity set, performing word segmentation on the corpus data and removing a stop word, so as to collect a context information set of each of the plurality of named entities;

combining context information sets of all the named entities in the named entity set to obtain an overall context information set of the named entity set;

conveying, based on the overall context information set of the named entity set, each of the plurality of named entities in the named entity set as an overall context information vector; and performing, based on the overall context information vector of the each of the plurality of named entities in the named entity set, the clustering process on all the named entities in the named entity set.

9. The synonym mining method according to claim 8, wherein the overall context information set of the named entity set is expressed as $\{x_t\}$, where $x_t$ represents a t-th word element in the overall context information set of the named entity set, t is an integer, $1 \leq t \leq T$, and T is a count of word elements in the overall context information set of the named entity set; and the conveying, based on the overall context information set of the named entity set, each of the plurality of named entities in the named entity set as the overall context information vector, comprises:

calculating a weight $y_t$ of the t-th word element $x_t$ in the overall context information set $\{x_t\}$ with respect to the each of the plurality of named entities, where t takes a value of 1, 2, . . . , and T in turn, and obtaining an overall context information vector ($y_1$, $y_2$, . . . , $y_T$) of the each of the plurality of named entities.

10. The synonym mining method according to claim 9, wherein a calculation formula of the weight $y_t$ of the t-th word element $x_t$ with respect to the each of the plurality of named entities is expressed as:

$$y_t = \frac{count(E, x_t)}{count(x_t)},$$

where E represents the each of the plurality of named entities, $count(x_t)$ represents a count of sentences comprising the t-th word element $x_t$ in the corpus data, and $count(E, x_t)$ represents a count of sentences comprising both the named entity E and the t-th word element $x_t$ in the corpus data.

11. The synonym mining method according to claim 9, wherein the performing, based on the overall context information vector of the each of the plurality of named entities in the named entity set, the clustering process on all the named entities in the named entity set, comprises:

taking each of the plurality of named entities in the named entity set as a candidate cluster, and taking the overall context information vector of the each of the plurality of named entities as a center vector of a corresponding candidate cluster; and performing the clustering process on all current candidate clusters until all the current candidate clusters cannot continue to be clustered, wherein the performing the clustering process on all the current candidate clusters comprises:

calculating an entity similarity between every two candidate clusters among all the current candidate clusters;

determining whether a maximum value of the entity similarities reaches a predetermined threshold;

if the maximum value of the entity similarities reaches the predetermined threshold, clustering two candidate clusters corresponding to the maximum value of the entity similarities into a new candidate cluster, taking an average of overall context information vectors of all named entities in the new candidate cluster as a center vector of the new candidate cluster, taking the new candidate cluster and remaining candidate clusters as all current candidate clusters, and continuing to perform the clustering process on all the current candidate clusters; and if the maximum value of the entity similarities does not reach the predetermined threshold, determining that all the current candidate clusters cannot continue to be clustered.

12. The synonym mining method according to claim 11, wherein a calculation formula of an entity similarity between any two candidate clusters is expressed as:

$$Sim(F_1, F_2) = \frac{V(F_1) \cdot V(F_2)}{|V(F_1)| \times |V(F_2)|},$$

where $V(F_1)$ and $V(F_2)$ represent center vectors of the any two candidate clusters, respectively, $V(F_1) \cdot V(F_2)$ represents a dot product of the center vectors $V(F_1)$ and $V(F_2)$ of the any two candidate clusters, and $|V(F_1)|$ and $|V(F_2)|$ represent modulus of the center vectors $V(F_1)$ and $V(F_2)$ of the any two candidate clusters, respectively.

13. The synonym mining method according to claim 1, further comprising:

constructing a synonym dictionary based on the synonym set corresponding to the each category.

14. An application method of a synonym dictionary, wherein the synonym dictionary is constructed by using the synonym mining method according to claim 13, and the application method comprises:

according to the synonym dictionary, performing a normalization process on a plurality of named entities which are synonyms in at least one text data, so as to convey the plurality of named entities which are synonyms with one named entity among the plurality of named entities which are synonyms.

15. A medical synonym mining method, comprising:

performing a recognition process on medical corpus data to obtain a medical named entity set of at least one category, wherein the medical named entity set of each category comprises a plurality of medical named entities;

performing a clustering process on the plurality of medical named entities in the medical named entity set of the each category to obtain a medical synonym candidate set corresponding to the each category;

performing, based on a word morphology similarity and a context similarity, a filtering process on the medical synonym candidate set corresponding to the each category to obtain a medical synonym set corresponding to the each category; and constructing a medical synonym dictionary based on the medical synonym set corresponding to the each category;

wherein the synonym candidate set comprises a plurality of synonym candidate clusters, and each of the plurality of synonym candidate clusters comprises a plurality of named entities; and the performing the filtering process on the synonym candidate set comprises:

performing the filtering process on the plurality of named entities in each of the plurality of synonym candidate clusters; and wherein the performing the filtering process on the plurality of named entities in the each of the plurality of synonym candidate clusters comprises:

randomly sorting the plurality of named entities in the each of the plurality of synonym candidate clusters to obtain a sorted candidate cluster set $\{e_i\}$, where $e_i$ represents an i-th named entity, i is an integer, $1 \leq i \leq K$, and K is a count of the named entities in the each of the plurality of synonym candidate clusters;

taking a first named entity $e_1$ as a first sub-cluster; and determining whether an m-th named entity $e_m$ can be added to one of existing n sub-clusters, if the m-th named entity $e_m$ can be added to a certain existing sub-cluster, adding the m-th named entity $e_m$ to the certain existing sub-cluster, and if the m-th named entity $e_m$ cannot be added to any existing sub-cluster, taking the m-th named entity $e_m$ as a new sub-cluster, where m takes a value of 2, 3, . . . , and K in turn, and n is a count of existing sub-clusters in a case where the m-th named entity is determined.

16. An application method of a medical synonym dictionary, wherein the medical synonym dictionary is constructed by using the medical synonym mining method according to claim 15, and the application method comprises:

according to the medical synonym dictionary, performing a normalization process on a plurality of medical named entities which are synonyms in at least one medical text data, so as to convey the plurality of medical named entities which are synonyms with one medical named entity among the plurality of medical named entities which are synonyms.

17. A synonym mining device, comprising:

a memory, configured to store computer readable instructions non-transitorily; and a processor, configured to execute the computer readable instructions, wherein upon the computer readable instructions being executed by the processor, the synonym mining method according to claim 1 is executed.

18. A storage medium, storing computer readable instructions non-transitorily, wherein upon the computer readable instructions being executed by a computer, the synonym mining method according to claim 1 is executed.

\* \* \* \* \*